(12) United States Patent
Cook et al.

(10) Patent No.: US 7,750,117 B2
(45) Date of Patent: Jul. 6, 2010

(54) METHODS FOR HEAT-STABILIZING PROTEINS WITH SPECIFIC BINDING ACTIVITIES

(75) Inventors: Mark E. Cook, Madison, WI (US);
Mingder Yang, Madison, WI (US);
Mark R. Etzel, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 790 days.

(21) Appl. No.: 10/777,825

(22) Filed: Feb. 11, 2004

(65) Prior Publication Data

US 2005/0175602 A1   Aug. 11, 2005

(51) Int. Cl.
*C07K 16/02* (2006.01)

(52) U.S. Cl. .................... 530/350; 530/359; 530/387.1; 426/55

(58) Field of Classification Search ........................ None
See application file for complete search history.

(56) References Cited

U.S. PATENT DOCUMENTS 2,950,204 A * 8/1960 Peebles ...................... 426/285
6,746,698 B2 * 6/2004 Freeman ....................... 426/2

OTHER PUBLICATIONS

Andya et al. The effect of formulation excipients on protein stability and aerosol performance of spray-dried powders of a recombinant humanized anti-IgE monoclonal antibody. Pharmaceutical Research (1999), 16(3), 350-358.*

Draber et al. Stability of monoclonal IgM antibodies freeze-dried in the presence of trehalose. J. of Immunlog. Methods. vol. 181, Issue 1, pp. 37-43 (Apr. 12, 1995).*
Edith A. Chenault. Guar Meal Could Be Used As Chicken Feed. AgNews News and Public Affairs Texas A&M University Agriculture Program; http://agnews.tamu.edu/dailynews/stories/POSC/Sep1302a.htm. Sep. 2002.
David Canovas, et al. Role of Ngamma-Acetyldiaminobutyrate as an Enzyme Stabilizer and an Intermediate in the Biosynthesis of Hydroxyectoine. Applied and Environmental Microbiology. Sep. 1999; vol. 65: 3774-3779.
Piero Carninci, et al. Thermostabilization and thermoactivation of thermolabile enzymes by trehalose and its application for the synthesis of full length cDNA. Proc. Natl. Acad. Sci USA; vol. 95, pp. 520-524. Jan. 1998.
Jose R. Meyer-Fernandes, et al. Allosteric effectors and trehalose protect larval Manduca Sexta fat body glycogen phosphorylase B against thermal denaturation, Insect Biochemistry and Molecular Biology 30 (2000) 473-478.
Teruko Toyoda, el al. Stabilization of Human Recombinant Erythropoietin through Interactions with the Highly Branched N-Glycans1. J. Biochem. 128, pp. 731-737 (2000).

* cited by examiner

*Primary Examiner*—Anish Gupta
(74) *Attorney, Agent, or Firm*—Armstrong Teasdale LLP

(57) ABSTRACT

It is disclosed here that a protein with a heat-labile specific binding activity can be stabilized with a saccharide compound with regard to the binding activity. To heat-stabilize the protein, it is mixed with a saccharide compound in a liquid suspension and the suspension is then dried to produce a solid that contains the protein and the saccharide. The saccharide compounds that possess the protein heat-stabilization activity include monosaccharides, disaccharides, polysaccharides, alkylated monosaccharides, alkylated disaccharides, alkylated polysaccharides, monosaccharide alcohols and alkylated monosaccharide alcohols.

8 Claims, 1 Drawing Sheet

METHODS FOR HEAT-STABILIZING PROTEINS WITH SPECIFIC BINDING ACTIVITIES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Many proteins such as various antibodies, receptors and peptides that have specific binding activities can be included in human and non-human animal food products or supplements as well as pharmaceutical and cosmetic products to achieve various beneficial effects by binding to the target biomolecules. However, the use of such proteins has been limited because many of the manufacturing processes for the above products involve a heating step during which the specific binding activities of the proteins are destroyed.

The above problem is well illustrated in the animal feed industry. Pelleted feed is preferred over feed mash because it has the advantage of less feed waste and improved ease of handling (Steven Leeson and John Summers, Commercial Poultry Nutrition ($2^{nd}$ ed.), p. 99, 1997, University Books, Guelph, Ontario, Canada). In addition, for the same amount of feed consumed, animals tend to spend less time and less energy eating pellets than feed mash, leading to higher feed efficiency (Leeson and Summers, p. 99). Pelleted feed is conventionally produced in pellet mills. To form pelleted feed, feed mash is first treated with steam and then passed through a die under pressure to form pellets (Leeson and Summers, p. 98). The pellets are then cooled quickly and dried by forced air. For the past twenty years, the temperature at which animal feed is pelleted has been raised from 71° C. to as high as 99° C. (Mike Coelho, Vitamin Stability in Premixes and Feeds: a Practical Approach, Proceedings of the BASF Technical Symposia, pp. 99-126, p. 104, May 25, 1994, Indianapolis, Ind.). Other methods available for processing feed mash, such as the extrusion method, the expander and compacter methods, and the thermal cooking method, all employ even higher temperatures than the steam pelleting method (Steven Leeson and John Summers, pp. 99-100, 1997). For example, the extrusion method which has been used to produce various pet foods and dry cereal snack foods employs a temperature of 121° C. to 149° C. (Mike Coelho, p. 100, 1994). Although various antibodies such as anti-phospholipase $A_2$ ($PLA_2$) and anti-CCK antibodies can be included in animal feed to promote animal growth and feed efficiency, the use of these antibodies have been limited to feed mash because they do not survive the high temperatures of the pelleting and extrusion processes. IgG is denatured at a temperature of 70° C. (Hajime Hatta et al., *Biosci. Biotech. Biochem.* 57:450-454, 1993).

Agents and methods that can heat-stabilize proteins and their binding activities at relatively high temperatures are desirable in the art.

BRIEF SUMMARY OF THE INVENTION

In one aspect, the present invention relates to a method for heat-stabilizing a protein having a specific binding activity. The method involves mixing the protein with a saccharide compound in a liquid suspension and drying the suspension to obtain a solid that contains the protein and the saccharide compound. In such a solid, the saccharide compound is operably associated with the protein molecules to protect the protein's specific binding activity from the destructive effect of heat. The saccharide compounds that possess the above protein stabilization activity include monosaccharides, disaccharides, polysaccharides, alkylated monosaccharides, alkylated disaccharides, alkylated polysaccharides, monosaccharide alcohols and alkylated monosaccharide alcohols.

In another aspect, the present invention relates to a method of reducing the loss of a specific binding activity of a protein during a process in which the protein is exposed to heat. The method involves heat-stabilizing the protein as described above and exposing the heat-stabilized protein to heat. The heat-stabilized protein-containing product, characterized by the higher specific binding activity of the protein in comparison to the corresponding product made with unstabilized protein, is also within the scope of the present invention.

It is an object of the present invention to provide a method for heat-stabilizing a protein having a specific binding activity.

It is an advantage of the present invention that many of the saccharide compounds that can be employed to heat-stabilize the protein are safe for consumption by a human or non-human animal.

DETAILED DESCRIPTION OF THE INVENTION

Figure 1:
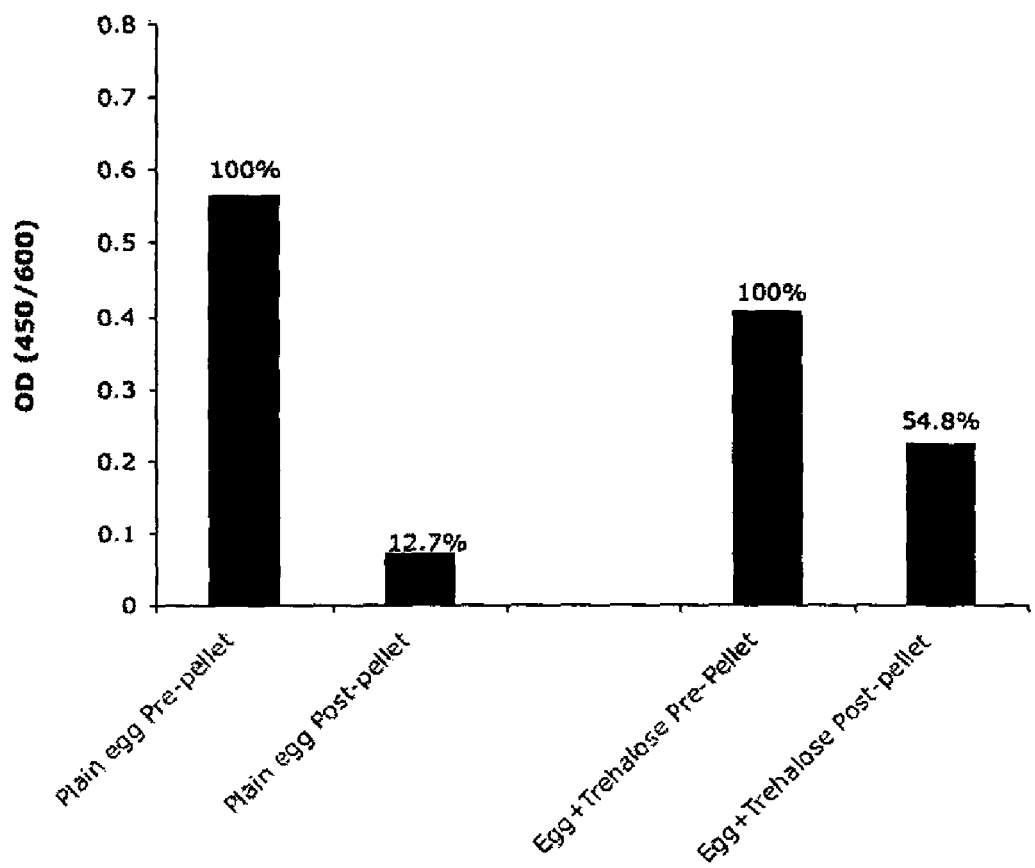
FIG. 1 shows the egg anti-$PLA_2$ antibody activity before and after the steam pelleting process in control and trehalose treated groups.

It is disclosed here that a heat-labile specific binding activity of a protein can be stabilized with a saccharide compound. By heat-stabilizing the binding activity of the protein, we mean that when compared to the corresponding unstabilized protein, the protein loses less of its binding activity upon being exposed to a binding-activity-destroying temperature, which is defined as a temperature at which the corresponding unstabilized protein will lose at least some of its binding activity. To heat-stabilize the specific binding activity of a protein, the protein is mixed with a saccharide compound in a liquid suspension and the suspension is then dried to produce a solid that contains the protein and the saccharide. The inventors found that the protein in such a solid can retain more of its binding activity after being exposed to a heat of a binding-activity-destroying temperature. The inventors believe that treating the protein as described above allows the saccharide compound to be operably associated with the protein molecules to protect the protein molecules from the destructive effect of heat. The inventors further found that the protein can be readily released from the association before or when it reaches a target site to achieve its biological activity. Using trehalose and chicken feed as examples, the inventors demonstrated in the examples below that associating trehalose to anti-$PLA_2$ antibodies reduced the loss of the antibodies' antigen binding activity during the steam pelleting process. Further, the antibodies were released from the association at the gastrointestinal tract to achieve the growth-promoting effect. In general, the present invention can be applied to benefit the human and non-human animal food industry, the human and non-human animal dietary or nutritional supplement industry, the pharmaceutical industry, the cosmetics industry, and other industries in which preserving the specific binding activity of a protein is of significance to a product manufactured through a process that involves binding-activity-destroying temperatures. For the purpose of the present invention, the terms "feed for non-human animal" and "food for non-human animal" are used interchangeably.

As used herein, a saccharide compound is "associated" with a protein molecule if the saccharide compound is directly or indirectly, physically or chemically bound to the protein molecules. As an example, a saccharide compound can be physically bound to a protein molecule by entrapping or encapsulating the protein molecule, or chemically bound to a protein molecule through ionic or hydrogen bond(s).

The saccharide compounds that possess the protein heat-stabilization activity include monosaccharides, disaccharides, polysaccharides, alkylated monosaccharides, alkylated disaccharides, alkylated polysaccharides, monosaccharide alcohols and alkylated monosaccharide alcohols. Monosaccharides are single sugar residues having the formula $(CH_2O)_n$ wherein n is 3 or bigger. Monosaccharides in all isomeric forms such as α-isomers, β-isomers, D-isomers and L-isomers have the activity. Examples of monosaccharides that can be used in the present invention include but are not limited to glucose, ribose, fructose, galactose, talose, arabinose, fucose, mannose, xylose and erythrose. Preferably, monosaccharides of 5 or 6 carbons are used in the present invention.

Disaccharides are molecules with two monosaccharide residues joined together by a glycosidic bond. Examples of disaccharides that can be used in the present invention include but are not limited to trehalose, maltose, sucrose, lactose, maltose and lactulose. Preferably, disaccharides formed by two monosaccharides of 5 or 6 carbons are used.

For the purpose of the present invention, polysaccharides are molecules with three or more monosaccharides linked together. The monosaccharides can form either linear, unbranched chains or branched chains. Starch, glycogen and cellulose are examples of polysaccharides having hundreds or even thousands of monosaccharide residues. Starch can contain either linear, unbranched chains (amylose) or highly branched chains (amylopectin). Glycogen contains branched chains and cellulose contains linear, unbranched chains. Preferably, polysaccharides formed by monosaccharides of 5 or 6 carbons are used in the present invention.

Alkylated monosaccharides, alkylated disaccharides and alkylated polysaccharides are monosaccharides, disaccharides and polysaccharides with at least one of the hydrogen groups substituted by an alkyl group. Preferably, alkylated saccharides based on monosaccharides of 5 or 6 carbons are used in the present invention.

Monosaccharide alcohols are acyclic polyols that contain three or more hydroxyl groups. They can be formed by converting the ketone or aldehyde groups of the monosaccharides to hydroxyl groups. Examples of monosaccharide alcohols include but are not limited to glycerine, mannitol, sorbitol, xylitol, lactitol, isomalt, maltitol, and hydrogenated starch hydrolysates. Preferably, monosaccharide alcohols based on monosaccharides of 5 or 6 carbons are used in the present invention.

Alkylated monosaccharide alcohols are monosaccharide alcohols with at least one of the hydrogen groups substituted by an alkyl group. Preferably, alkylated monosaccharide alcohols based on monosaccharides of 5 or 6 carbons are used in the present invention.

Any protein with a heat-labile specific binding activity can be heat-stabilized by a saccharide compound described above. A protein with a specific binding activity means that the protein binds to its target molecule with a dissociation constant $(K_d)$ of $10^{-3}$ M or less. Examples of such proteins include but are not limited to antibodies (bind to antigens) and receptors (bind to natural or non-natural ligands and agonists and antagonists of the ligands). Other examples of such proteins are soluble fragments of receptors that contain the ligand binding domains. Such fragments can compete with the ligands for binding to the receptors.

A protein with a specific binding activity can be mixed with a saccharide compound in any liquid suspension in which the protein and saccharide compounds are sufficiently dispersed in the suspension so that when the suspension is dried, the saccharide compound is operably associated with the protein molecules. Examples of the liquid suspensions that can be used in the present invention include but are not limited to solutions, colloids and emulsions. All suitable methods available in the art for drying liquid suspensions can be readily used by a skilled artisan to practice the present invention. Negative pressure and inert gas streams are often employed in these methods to assist the drying process.

In one aspect, the present invention relates to a method for heat-stabilizing a protein having a specific binding activity. The method involves mixing the protein with a saccharide compound in a liquid suspension and drying the suspension to obtain a solid that contains the protein and the saccharide compound. An improvement in heat stability of the protein provided in such a solid can be evaluated by measuring the specific binding activity retained after being exposed to a binding-activity-destroying temperature and comparing it to that of the corresponding unstabilized protein. In this regard, any suitable assays such as an ELISA assay can be used to measure the binding activity of the protein. In a preferred embodiment, the heat-stabilized protein will maintain or lose less of its binding activity in comparison to the corresponding unstabilized protein when exposed to a heat of at least 70° C., 80° C., 90° C., 100° C., 110° C., 120° C., 130° C., 140° C. or 150° C. In another preferred embodiment, at least 10%, 20%, 30%, 40%, 50%, 60%, 70%, 80% or 90% of the binding activity prior to heat exposure is retained after heat exposure.

In another aspect, the present invention relates to a method of reducing the loss of a specific binding activity of a protein during a process in which the protein is exposed to a binding-activity-destroying temperature. The method involves heat-stabilizing the protein as described above and exposing the heat-stabilized protein to the binding-activity-destroying temperature. The end product of the process, which contains the protein and characterized by the higher specific binding activity of the protein in comparison to the corresponding product made with the unstabilized protein, is also within the scope of the present invention. Examples of the processes during which the specific binding activity of a protein can be protected include but are not limited to processes for making human and non-human animal food products or supplements, pharmaceutical products and cosmetic products.

In one embodiment, the present invention is practiced in connection with an animal feed processing method in which the animal feed is exposed to a binding-activity-destroying temperature. Examples of such animal feed processing methods include but are not limited to the steam pelleting method, the extrusion method and the expander or compactor method. In a preferred embodiment, an antibody produced in a chicken egg is added to an animal feed for processing. Antibodies in a chicken egg can be heat-stabilized by mixing the egg white and egg yolk and then adding and mixing a saccharide compound in the resulted egg liquid suspension, followed by spray drying the egg liquid suspension to obtain a powder that contains the antibodies and the saccharide compound. Preferably, the saccharide compound in the amount of 5% to 30% of the egg liquid (by weight), and more preferably in the amount of 10% to 20% of the egg liquid (by weight), is added into the egg liquid for mixing. In other applications, the suitable amount of a saccharide that can be added into a liquid suspension for effectively heat-stabilizing a protein can be readily determined by a skilled artisan through routine experimentation. The powder containing the heat-stabilized egg antibodies can then be mixed and processed with the animal feed. To make feed pellets, for example, the animal feed is treated with steam and then passes through a die under pressure to form pellets. The pellets are then cooled quickly and dried by means of forced air.

The following examples are given to further illustrate the present invention. The present invention is not limited to the specific details set forth in the examples.

EXAMPLE 1

Trehalose and a Combination of Sucrose and Starch Reduced the Loss of Antigen Binding Activity of $PLA_2$ Antibody Materials and Methods Egg anti-$PLA_2$ antibody was produced by injecting three hundred 20-week-old laying hens with antigen $PLA_2$ (Sigma, St. Louis, Mo.). Antigen was prepared by emulsifying equal volume of antigen solution (200 μg/ml) with Freund's adjuvant (Sigma). Each hen was injected intramuscularly with a total of 1 ml emulsified $PLA_2$ (each of the two thighs and two breasts was injected with one 0.25 ml inoculum). Freund's complete adjuvant was used only in the first inoculation and Freund's incomplete adjuvant was used in the later injections. Second inoculation was one week after the first inoculation and the subsequent inoculation was two months apart.

Birds were checked daily for morbidity and mortality. Egg production was also recorded daily. Eggs from hens inoculated with $PLA_2$ were collected starting at day 21 after the first inoculation. Eggs were then broken and gently mixed by a mixer to mix egg white and egg yolk. Sugar powder (trehalose or a combination of sucrose and starch) was dissolved in warm water and the sugar solution was then added and mixed into liquid eggs. The percentage of trehalose added was 12% of the liquid eggs (by weight) and the percentage of the combination of sucrose and starch added was 6% sucrose and 6% starch of the liquid eggs (by weight). Sugar was added to protect egg yolk antibody from heat and humidity throughout the subsequent processing procedures including spray-drying and animal feed pelleting. The liquid egg-sugar solution was then spray-dried with a food grade dryer. The drying temperature was 90° C.

After spray drying, egg powder (contains trehalose) was shipped to a commercial broiler farm for pelleting testing. Egg powder was added into commercial mash feed which then passed through a commercial feed pelleting machine where the pelleting temperature was 82.2° C. and the mash feed stayed in the steam chamber for about 10-12 seconds. Feed samples were taken before and after the pelleting process. Established ELISA method was used to determine the antigen binding activity of the egg yolk antibody before and after the pelleting process.

Results

As shown in FIG. 1, without trehalose protection, only 12.7% of the binding activity of anti-PLA2 antibody in mash feed was left after the pelleting process. With trehalose protection (12% in liquid egg by weight), the antibody retained 54.8% of its binding activity. In a parallel experiment where a combination of 6% sucrose and 6% starch (in liquid egg by weight) was employed to protect the anti-$PLA_2$ antibody, a reduction in binding activity loss during the pelleting process was also observed. However, this combination was not as effective as 12% trehalose. In two similar experiments, the inventors observed that the antibodies retained over 65% and 80% of their pre-pelleting binding activities after the pelleting process.

EXAMPLE 2

Animal Feed Pellets Containing Trehalose Protected $Pla_2$ Antibodies Were Effective to Promote Animal Growth Materials and Methods A total of 954 broiler chickens were randomly assigned to either a control group or a $PLA_2$ antibody group and their body weights were recorded. In the control group, birds received standard commercial pellet feed. In the $PLA_2$ antibody group, the pellet feed was formulated to contain 0.125% (by weight) sugar-associated $PLA_2$ antibody egg powder and produced with trehalose as described in Example 1. Birds were kept on the above diets for 4 weeks and their body weights were recorded at the end of the 4 weeks.

Results

As expected from random assignment, the average body weights of the control and $PLA_2$ groups were the same at the beginning of the trial (data not shown). At the end of the trial, the average body weight of $PLA_2$ antibody group was higher than that of the control group (p<0.01). Therefore, by stabilizing the $PLA_2$ antibody with trehalose, chicken feed containing the antibody can be pelleted and fed to chickens without losing the antibody's beneficial effect of promoting growth.

TABLE 1

|  | Average Body Weight (lb) | % change |
| --- | --- | --- |
| Control | 2.35 |  |
| $PLA_2$ antibody | 2.41 | 2.55 |

The present invention is not intended to be limited to the foregoing examples, but to encompass all such modifications and variations as come within the scope of the appended claims.

We claim:

1. A method for producing a feed containing heat-stabilized egg antibodies, the method comprising the steps of:
   mixing an egg white, an egg yolk and at least one saccharide selected from a monosaccharide, a disaccharide, a polysaccharide, an alkylated monosaccharide, an alkylated disaccharide, an alkylated polysaccharide, a monosaccharide alcohol, or an alkylated monosaccharide alcohol to form an egg liquid suspension, said egg yolk containing an egg antibody produced in response to antigen inoculation; and
   spray drying the egg liquid suspension to form an egg powder; and
   processing the egg powder to provide a feed containing heat-stabilized egg antibodies, said processing step including exposing the egg powder to an antigen-binding-activity-destroying temperature of at least 70° C;

wherein the heat-stabilized egg antibodies in the feed produced by said method loses less of its antigen-binding activity in comparison to an egg yolk antibody retaining at least 20% of its antigen-binding activity after being exposed to said antigen-binding-activity-destroying temperature.

2. The method of claim 1, wherein the saccharide compound is selected from a monosaccharide of 5 or 6 carbons, a disaccharide made of monosaccharide residues of 5 or 6 carbons, and a polysaccharide made of monosaccharide residues of 5 or 6 carbons.

3. The method of claim 2, wherein the polysaceharide contains linear, unbranched chains.

4. The method of claim 1, wherein the saccharide compound is selected from an alkylated monosaccharide of 5 or 6 carbons, an alkylated disaccharide made of alkylated monosaccharide residues of 5 or 6 carbons, and a polysaccharide made of alkylated monosaccharide residues of 5 or 6 carbons.

5. The method of claim 1, wherein the monosaccharide alcohol has 5 or 6 carbons.

6. The method of claim 1, wherein the feed is selected from a animal feed product and a non-human animal dietary nutritional supplement.

7. The method of claim 6, wherein the product is an animal feed product.

8. The method of claim 7, wherein the animal feed product is a feed pellet.

* * * * *